United States Patent [19]

Gregory et al.

[11] Patent Number: 5,074,860

[45] Date of Patent: * Dec. 24, 1991

[54] APPARATUS FOR DIRECTING 10.6 MICRON LASER RADIATION TO A TISSUE SITE

[75] Inventors: Christopher C. Gregory, Highland Park; James A. Harrington, Martinsville, both of N.J.

[73] Assignee: Heraeus LaserSonics, Inc., Milpitas, Calif.

[*] Notice: The portion of the term of this patent subsequent to Mar. 27, 2007 has been disclaimed.

[21] Appl. No.: 364,903

[22] Filed: Jun. 9, 1989

[51] Int. Cl.⁵ .............................................. A61B 17/36
[52] U.S. Cl. ..................................... 606/14; 128/395; 128/6; 606/13; 385/125; 385/117
[58] Field of Search .................................. 606/2, 10–19; 128/4–6, 303.1, 395–398; 350/96.3, 96.32

[56] References Cited

U.S. PATENT DOCUMENTS

| | | | |
|---|---|---|---|
| 4,545,713 | 10/1985 | Beni et al. | 606/19 X |
| 4,583,526 | 4/1986 | Ali | 606/15 X |
| 4,583,539 | 4/1986 | Karlin et al. | 606/19 X |
| 4,589,729 | 5/1986 | Bridges et al. | |
| 4,592,353 | 6/1986 | Daikuzono | 606/17 X |
| 4,597,380 | 7/1986 | Raif et al. | 606/14 X |
| 4,638,801 | 1/1987 | Daly et al. | 606/10 X |
| 4,911,712 | 3/1990 | Harrington | 606/14 |
| 4,917,083 | 4/1990 | Harrington et al. | 606/15 |

Primary Examiner—Robert A. Hafer
Assistant Examiner—Kerry Owens
Attorney, Agent, or Firm—Flehr, Hohbach, Test, Albritton & Herbert

[57] ABSTRACT

A $CO_2$ (10.6 micron) medical delivery end probe is described which enables line-of-sight viewing of a surgical site internally within a body within the very same endoscope used to house the probe. The end probe includes two different sections of $n<1$ air core hollow waveguides, obliquely related to one another. A mirror is positioned to reflect radiation from the exit end of the initial guide to the entry end of the main section. A bridge which is especially adapted for use in an endoscope with both such a probe and a telescope is also described. Moreover, an adapter having the initial optical guide section discussed above enabling straight end probes to be used is also described.

21 Claims, 4 Drawing Sheets

APPARATUS FOR DIRECTING 10.6 MICRON LASER RADIATION TO A TISSUE SITE

The present invention relates to laser medical systems and, more particularly, to the delivery of 10.6 micron radiation to a tissue site for surgery in a manner which is conducive to straight telescopic and unaided line-of-sight viewing of the surgical operation.

BACKGROUND OF THE INVENTION $CO_2$ (carbon dioxide) laser radiation is widely used to create surgical incisions internally of a human body. While the principal component of $CO_2$ radiation, i.e., 10.6 microns in wavelength, interacts favorably with tissue for surgery, it is not a straight forward process to deliver the same efficiently to a surgical site. U.S. patent application Ser. No. 07/164,236, filed Mar. 4, 1988, the disclosure of which is hereby incorporated herein by reference and which is owned by the assignee of this application is directed to a method and arrangements found to be particularly useful for delivering such radiation. U.S. patent application Ser. No. 07/181,448, filed Apr. 14, 1988 owned by the same assignee and naming, like the above application, one of the inventors herein, is directed to an end probe which takes advantage of using the conditions discussed below in a hollow waveguide made from a single crystal material.

There is an anomalous dispersion phenomenon that is associated with transmission of 10.6 micron radiation. As pointed out in the paper entitled "Dispersion Phenomena in Hollow Alumina Waveguides" (1985) authored by Jenkins, et al. and appearing at pages 1722, et seq. of the *IEEE Journal of Quantum Electronics*, Vol. QE-21, it has been discovered that the attenuation of 10.6 micron radiation by a hollow air core alumina waveguide is significantly lower than it is for other longer or shorter wavelengths. This phenomenon has been associated with the index of refraction (n) of the waveguide for 10.6 micron radiation. That is, this unexpected phenomenon has been associated with the index of refraction of the cladding of a hollow air core waveguide being less than one, the index of refraction of air, at such wavelength. A hollow waveguide of the type to which the invention relates is commonly referred to as a "$n<1$" waveguide.

As mentioned previously, 10.6 micron radiation is used for internal surgery. It is important that a physician implementing such surgery within a body have a view of the surgery which he or she is performing. Generally, such visualization is achieved by locating a viewing telescope or a fiber optic viewing probe at the surgical site. In many of such applications, an endoscope is used both to house a radiation delivery probe and a viewing telescope or fiber optic device. For example, in gynecology, a laparoscope (a specialized endoscope) can be used to house both an $n<1$ waveguide and a right angle offset viewing telescope. In many medical applications, however, a surgeon often wishes to view a treatment site by the unaided eye in a line-of-sight manner or by using a straight telescope. Specifically, a straight rod-lens telescope is placed in the central lumen of, for example, a bronchoscope. It will be recognized that it is impractical to also use such a bronchoscope to deliver $CO_2$ radiation to the site in a conventional manner, i.e., by focusing the radiation to a small spot at the distal end of the bronchoscope. Since the free laser beam would occupy the entire central lumen of the endoscope, there is no space for introducing other instruments, such as a viewing telescope, down the endoscope while the laser is in use. Also, the walls of the central lumen of a typical endoscope will not efficiently guide $CO_2$ radiation. Thus, it is quite advantageous for one to be able to use an $n<1$ waveguide to convey the $CO_2$ radiation to the surgical site since such conveyance does not rely on the endoscope except as a protective device. The difficulty, though, is that with $n<1$ guides and other delivery systems for 10.6 micron radiation that only utilize the endoscope as a protective housing, the construction of the same has resulted in obstruction of straight or line-of-sight viewing through the endoscope, with the result that their use is not as widely applicable as desired. While at first blush it would appear that a right-angle coupler of a standard design could be used to couple 10.6 micron radiation from a delivery system to an $n<1$ guide, it is recognized by those skilled in the art that the bulky construction of a conventional coupler will provide the same obstruction problems.

SUMMARY OF THE INVENTION

It has been discovered that the principles associated with an $n<1$ waveguide can be utilized to minimize the constructional size of those parts of a delivery system which would have in the past obstructed line-of-sight or straight viewing through an endoscope. More particularly, the invention includes an end probe for delivering $CO_2$ radiation to a surgical site within a body, which probe has at least two sections which are oblique to one another, the initial section being a hollow waveguide having a cladding index of refraction which is less than its core for radiation having a wavelength of 10.6 microns, i.e., $n<1$ waveguide section if the core is an air core. It has been found that use of such an initial $n<1$ section to convey the radiation in a waveguide manner, rather than allow the radiation to be conveyed simply in a focusing manner as has been done in the past, enables the radiation to be delivered right to a mirror or other reflecting surface to provide reflection for a sharp change of direction. That is, use of an $n<1$ waveguide section to provide direct conveyance of the radiation eliminates the transverse spacing (spacing transverse to the optic axis) typically necessary in a conventional lens focusing system.

An end probe is provided in keeping with the invention having two optical guide sections which are oblique to one another, preferably at 9°. At least the initial section is a hollow waveguide having a cladding index of refraction less than that of its core. This facilitates providing minimal constructional portions exterior of the waveguide which are typically associated with bending of an optic axis of $CO_2$ radiation. This also minimizes the bulk of the portion of the probe which has to traverse the endoscope. Most desirably, both sections are $n<1$ hollow waveguides.

The principles of the invention are also incorporated in an adapter which enables its use with standard, straight probes. Such adapter also includes an initial guide section which is a hollow waveguide having a cladding index of refraction less than that of its core. However, instead of a second optical guide section it includes a socket for receiving an end probe and orienting the same obliquely to the initial guide section to receive the initial radiation. The initial waveguide section also is most desirably an air core, $n<1$ hollow waveguide.

The invention also includes a bridge designed to hold both a telescope and a probe in proper relationship to one another within an endoscope. The bridge most desirably also includes an evacuation tube for directing smoke and the like from the tissue site back through the endoscope. Moreover, the telescope and the end probe are slidably received within the bridge to permit appropriate focusing and the like.

The invention includes other features and advantages which will be described or will become apparent from the following more detailed description of preferred embodiments.

BRIEF DESCRIPTION OF THE DRAWINGS

With reference to the accompanying four sheets of drawing.

DETAILED DESCRIPTION OF PREFERRED EMBODIMENTS

Figure 1:
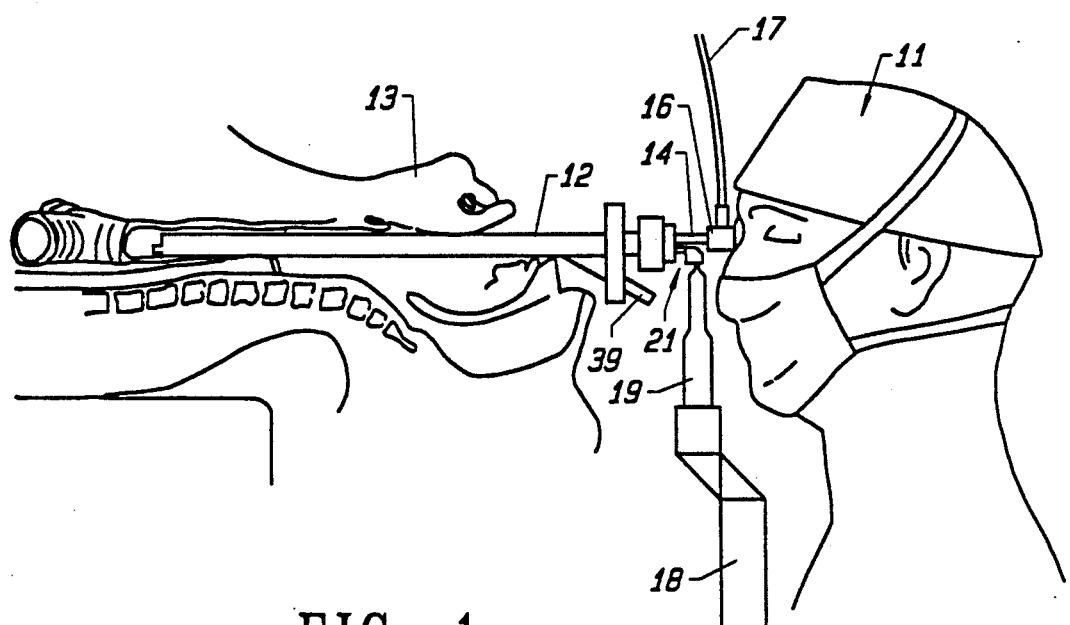
FIGS. 1 and 2 respectively are side and top elevation and plan views of a surgeon utilizing the instant invention to ablate a lesion, tumor or other tissue in the bronchi.
Figure 2:
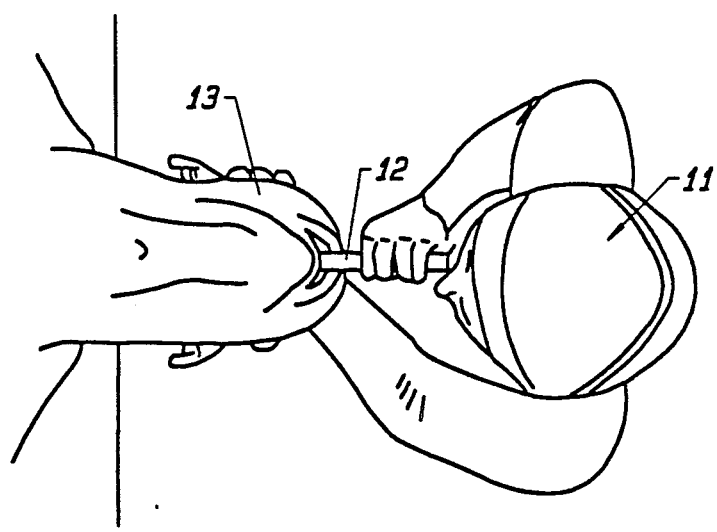
Figure 3:
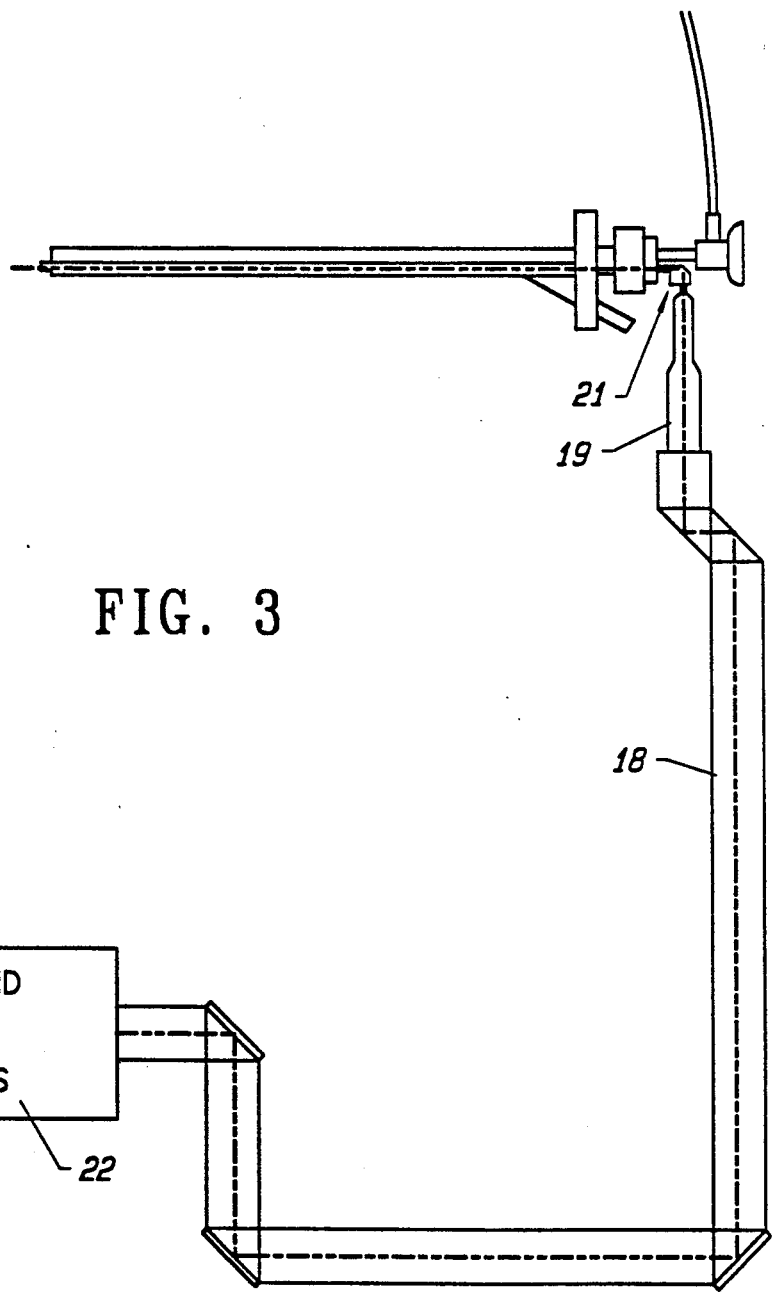
FIG. 3 is an overall view of the radiation delivery system of FIGS. 1 and 2.

Reference is first made to FIGS. 1 through 3 which illustrate a preferred embodiment of the invention. FIGS. 1 and 2 show the same being utilized to ablate a lesion, tumor or other tissue in the bronchi of a patient. A surgeon indicated by the reference numeral 11 is illustrated utilizing a bronchoscope 12 (a specialized form of an endoscope—As used herein, the term "endoscope" is a generic term meaning any tubular member which is insertable within a body cavity to provide a housing to separate medical instrumentation and the like from the body). Such bronchoscope extends through the mouth of a patient 13 through his/her throat to the bronchial tree. The bronchoscope 12 is, in essence, a tube having a right circular cylinder cross section taken at 90° to its longitudinal axis.

It is common and desirable in those $CO_2$ radiation surgical operations in which a bronchoscope is used, that the physician have line-of-sight or straight telescopic viewing of the surgical procedure. To this end, a straight rod-lens telescope 14 extends through the bronchoscope to the site. In keeping with the invention, ah end probe is used which will not obstruct straight viewing and prevent the use of such telescope (as will be discussed in more detail below). Thus, the telescope terminates as is common with an eye piece 16 which is utilized by the physician as illustrated for viewing the surgical site. A typical illumination mechanism is provided as part of the telescope, indicated in the drawings by the illumination bundle 17.

It can be seen from FIGS. 1 and 2 how the end probe of the invention enables straight viewing through the endoscope while yet providing precise delivery of the radiation through use of, for example, $n<1$ hollow waveguide radiation transmission to the site. The desired 10.6 micron radiation is transmitted through an articulated arm 18 to a coupler 19 for delivery to an end probe, generally referred to by the reference numeral 21, of the invention. 10.6 micron radiation produced by a $CO_2$ laser and an aiming beam produced by a HeNe laser are introduced into the articulated arm at its proximal end as is represented in FIG. 3 at 22. Most desirably, the laser delivery system is the same as that described in U.S. patent application Ser. No. 07/164,236 mentioned earlier.

Figure 4:
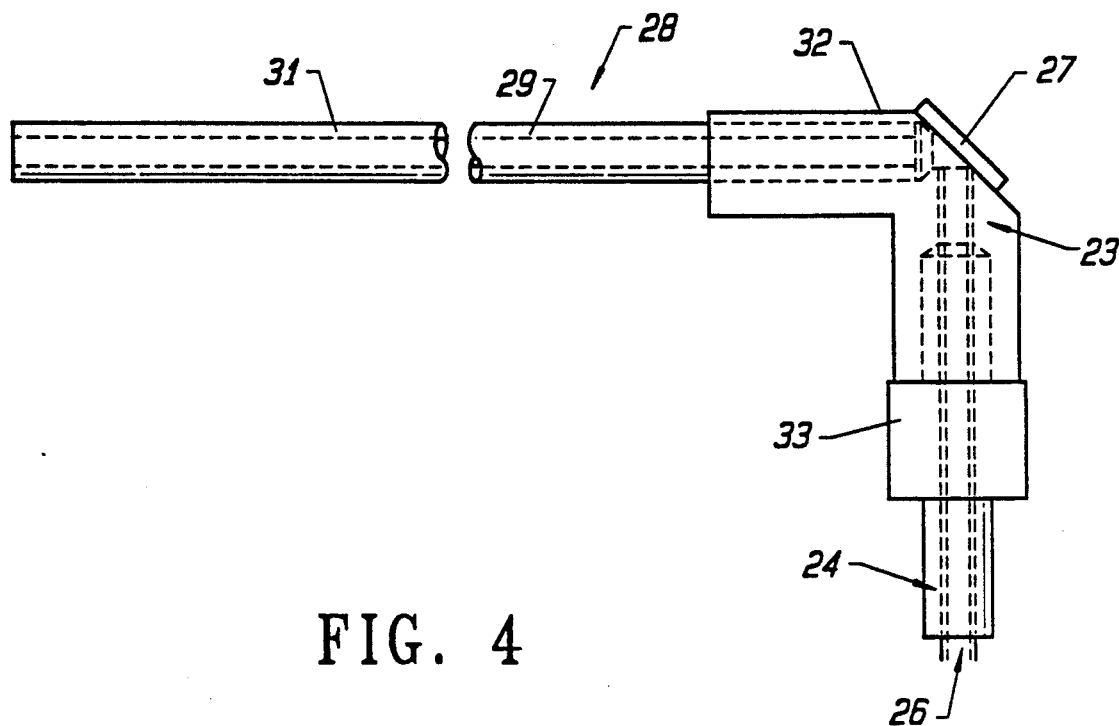
FIG. 4 is a broken-away side view illustrating an end probe of the invention.

The end probe 21 of the invention is illustrated in more detail in FIG. 4. It includes an initial guide section 23 which is positioned to receive radiation from the coupler 19 and guide it between its ends. It is a hollow waveguide having a cladding 24 and a core 26, the index of refraction of the cladding being less than that of the core at the wavelength of 10.6 microns. 10.6 micron radiation will be coupled to the entry end of section 23 as long as the criteria set forth in patent application Ser. No. 07/164,236, the disclosure of which is incorporated herein by reference, is followed. In this connection, the coupling f number at the entry end preferably is in the range of about f/15 to f/25. The initial guide section 23 directs the radiation to a mirror 27 which reflects the same to the entry end of a main optical section 28, without material radiation loss or a change in the mode characteristic of such radiation. If the initial guide section receives single-mode radiation, such radiation will diverge very slowly at its exit end (divergence angle $\approx$ about 3°).

The main optical section is oblique, 16 preferably 90°, to the initial guide section as illustrated. It also most desirably is an $n<1$ waveguide so that the precision associated with delivery of 10.6 micron radiation is not lost. Moreover, if the main optical guide section is not a hollow waveguide having a cladding index of refraction less than that of the core at 10.6 microns, the miniaturization feature of the instant invention may be lost. The main optical guide section therefore also includes a cladding 29 and a hollow air core 31.

It should be noted that while in this preferred embodiment the main guide section is integral from its proximal end to its distal end, the invention is equally applicable to arrangements in which the main guide section is made up of two components, e.g., a disposable tip and a non-disposable portion.

It should be noted that the mirror 27 also reflects the aiming beam. This beam is not transmitted by the waveguide sections as efficiently as the $CO_2$ beam, though, since for HeNe radiation, the aiming beam radiation, the index of refraction of the two guide sections is greater than one.

The housing 32 for the joining ends of the sections and mirror 27 can be made, and is made, quite small in order to avoid interfering with a straight telescope or unaided line-of-sight viewing. That is, because of the $n<1$ hollow waveguide conveyance to the mirror 27 or other reflecting means, it is not necessary that the housing be any larger than needed to accommodate the lateral extent of the guide sections and the mechanical coupler 33 for connecting the same to the optical coupler 19. The location of the mirror 27 exteriorly of the housing as illustrated enhances this miniaturization.

Figure 5:
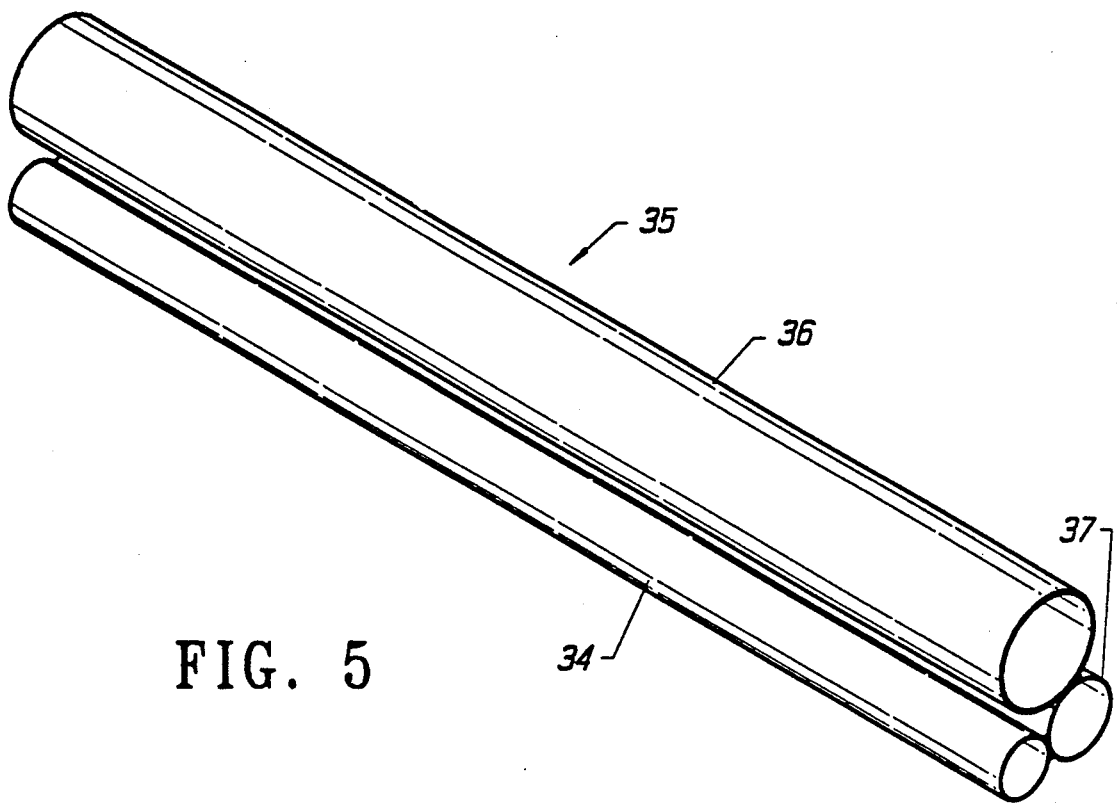
FIG. 5 is an isometric view of a bridge of the invention for an endoscope.
Figure 6:
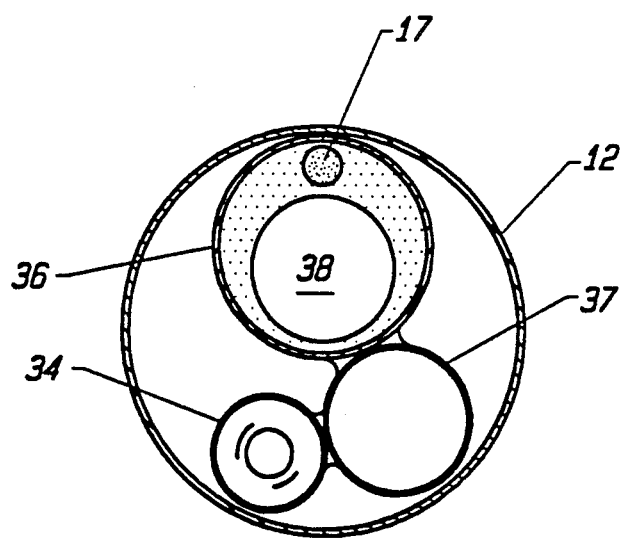
FIG. 6 is a sectional view showing the bridge of the invention and its relationship to an endoscope, a straight telescope and an $n<1$ hollow waveguide.

The invention includes not only the end probe itself, but the structural combination of the end probe, an endoscope through which the probe extends, and a straight telescope also extending through the endoscope with the probe. Most desirably, a bridge generally referred to by the reference numeral 35, is included which is designed to facilitate such combination. FIG. 5 illustrates such bridge and FIG. 6 shows how the same enhances the combination discussed above, provides for smoke and the like evacuation through the endoscope and assures steady air or other gas delivery to the surgical site. Guide 35 is most simply a plurality of parallel tubes, one of which, tube 34, is designed to carry the main section of the end probe, another of which, tube 36, is designed to carry the straight telescope, and a third one of which, tube 37, is designed to provide evacuation from the surgical site. Such tubes are made from an appropriate material, such as stainless steel, and are connected together along their length by, for example, brazing. Tube 34 acts as a protective housing for the main section of the end probe once the end probe is installed in the same. Moreover, it maintains the longitudinal optic axis of such probe section parallel to the longitudinal optic axis of the telescope. Most desirably, the waveguide is slidably received within the guide so that its distance from the surgical site easily can be adjusted without interfering with the distance adjustment of the telescope.

The tube 36 contains the illumination bundle 17 as well as the optics (indicated by space 38 in FIG. 6) for the telescope. It also is most desirably slidably received within the bridge to enable its distance to be adjusted from the surgical site for, for example, focusing and the like.

As illustrated, the bridge 35 is spaced from the inner wall of the bronchoscope 12 to define air or other gas passageways through the endoscope. In this connection, a standard connection 39 is provided for introducing anesthesia or the like to the bronchoscope. Appropriate sealing (not shown) is provided in a conventional manner to assure containment of anesthetic gases if it is desired that such gases flow in the spaces within the endoscope not taken up by the bridge 35 and its contents.

It will be appreciated from the above that only one hand of the surgeon is required to support the combination. It is also removable from the patient as a unit.

Figure 7:
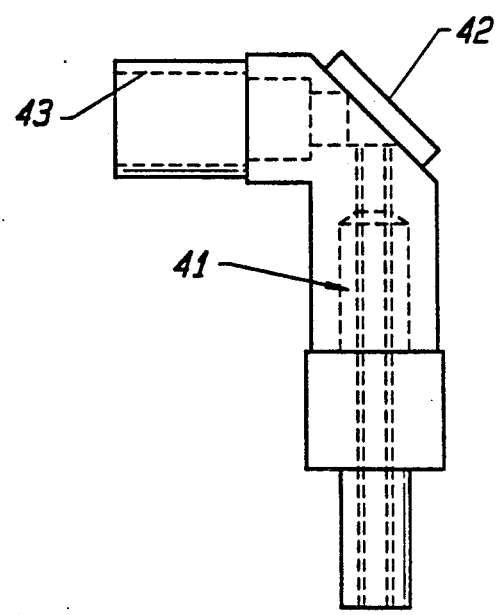
FIG. 7 is a side view illustrating an adapter of the invention.

The invention also includes an adapter to enable existing straight probes to take advantage of the invention. Such adapter is shown in detail in FIG. 7. It includes an initial optical guide section 41 which is essentially the same as the initial optical guide section 23 of the end probe described previously. It also includes a reflecting mirror 42 for reflecting radiation received from the distal end of the guide 41. However, instead of reflecting the same into (or through) a main probe section, it reflects the same to a socket indicated at 43 for receiving a standard straight end probe and orienting the same obliquely to the initial guide section. Socket 43 most desirably is sized to enable close positioning of the probe to mirror 42. The adapter thus enables the existing straight end probes to be utilized with the invention.

It will be appreciated by those skilled in the art that various changes and modifications can be made without departing from the spirit of the invention. It is therefore intended that the coverage afforded applicant be determined by the claims and their equivalents.

What is claimed is:

1. In apparatus for directing radiation having a wavelength of 10.6 microns from a source of such radiation to adjacent a tissue site within a body, an end probe for delivering such radiation to said tissue site without obstructing viewing of such site comprising:

a. an initial optical guide section for receiving said radiation at one end thereof and guiding it to a second end;
   b. a main optical guide section oriented obliquely to said initial guide section with a first end thereof positioned to receive radiation from said second end of said initial guide section and convey the same to a delivery end thereof at said tissue site; and
   c. at least said initial optical guide section being a hollow waveguide having a cladding and a core, the index of refraction of said cladding being less than that of said core at said wavelength of 10.6 microns.

2. The apparatus of claim 1 further including, in combination, a linear endoscope circumscribing said main guide section of said end probe; and a straight telescope extending through said endoscope with said main guide section.

3. The apparatus of claim 2 wherein said telescope and said main guide section each have a longitudinal optic axis, and a bridge is positioned within said linear endoscope to maintain said optic axes generally parallel to one another therewithin.

4. The apparatus of claim 1 wherein said main optical section is an integral material extending from said first end to the delivery end thereof.

5. The apparatus of claim 1 wherein both said initial and said main guide sections are hollow waveguides, each of which has a cladding whose index of refraction is less than that of the core thereof at said wavelength of 10.6 microns.

6. The apparatus of claim 5 wherein the hollow portion of each of said guides has a transverse section which is a generally right circular cylinder, and the inner diameter of said initial guide section is larger than the inner diameter of said main guide section.

7. The apparatus of claim 5 wherein both of said sections are air core hollow waveguides and the index of refraction of the cladding of each is less than 1.

8. The apparatus of claim 7 wherein the cladding of both of said guide sections is aluminum oxide.

9. The apparatus of claim 8 wherein said cladding of both of said sections is alumina.

10. The apparatus of claim 7 further including means at said second end of said initial guide section for reflecting radiation having a wavelength of 10.6 microns to said first end of said main optical guide section.

11. The apparatus of any of the previous claims further including, in combination with said end probe, an articulated arm coupled to a laser to receive radiation generated thereby and direct the same via articulations to an output end of said arm, and a coupler positioned to receive laser radiation emanating from the output end of said articulated arm and condition the same for receipt at the entry end of said end probe.

12. In apparatus for directing radiation having a wavelength of 10.6 microns from a source of such radiation to adjacent a tissue site within a body, an adapter for a probe for delivering such radiation to said tissue site without obstructing viewing of such site comprising:

a. an initial optical guide section for receiving said radiation at one end thereof and guiding it to a second end;
   b. means in combination with said initial optical guide section for receiving an end probe and orienting the same obliquely to said initial guide section with a first end thereof positioned to receive radiation from said initial guide section and convey the same to a delivery end of said end probe positioned at said site; and c. said initial optical guide section being a hollow waveguide having a cladding and a core, the index of refraction of said cladding being less than that of said core at said wavelength of 10.6 microns.

13. The apparatus of claim 12 wherein said initial optical guide section is an air core hollow waveguide having cladding circumscribing said air core that has an index of refraction less than 1 for 10.6 micron radiation.

14. The apparatus of claim 13 wherein said cladding is alumina.

15. The apparatus of claim 13 further including means at said second end of said initial guide section for reflecting radiation having a wavelength of 10.6 microns to said socket for receipt by a first end of an end probe positioned thereby.

16. The apparatus of any of claims 12, 13, 14 or 15 further including, in combination with said adapter, an articulated arm coupled to a laser to receive radiation generated thereby and direct the same via articulations to an output end of said arm, and a coupler positioned to receive laser radiation emanating from the output end of said articulated arm and condition the same for receipt at the entry end of said initial optical guide section.

17. In apparatus for directing radiation having a wavelength of 10.6 microns from a source of such radiation to adjacent a tissue site within a body, a structural combination for delivery such radiation to said tissue site and providing viewing of such site, the combination comprising:

a. a waveguide for delivering such radiation to said tissue site;

b. an endoscope having a linear portion circumscribing a section of said probe having a linear optic axis; and c. a straight telescope extending through said endoscope with said section of said probe, said telescope being movable in said endoscope independently of said waveguide.

18. In apparatus for directing radiation having a wavelength of 10.6 microns from a source of such radiation to adjacent a tissue site within a body, a structural combination for delivery such radiation to said tissue site and providing viewing of such site, the combination comprising:

a. an end probe for delivering such radiation to said tissue site;

b. an endoscope having a linear portion circumscribing a section of said probe having a linear optic axis;

c. a straight telescope extending through said endoscope with said linear section of said probe; and d. a bridge within said linear endoscope to maintain said optic axes generally parallel to one another.

19. The apparatus of claim 18 wherein said telescope is slidably received within said bridge along its linear optic axis.

20. The apparatus of claim 18 wherein said bridge defines an evacuation tube for directing smoke and the like from said tissue site through said endoscope.

21. The apparatus of claim 18 wherein said bridge comprises three parallel tubes, each of which has a transverse section which generally is a right circular cylinder, one of which is sized to carry said section of said end probe, another of which is sized to carry said telescope and the third of which defines said evacuation tube; said bridge fitting within said endoscope to be spaced at least partially from the inner wall thereof to provide space for the flow of gas through said endoscope to said tissue site.

* * * * *